United States Patent
Moon et al.

(10) Patent No.: US 9,107,686 B2
(45) Date of Patent: Aug. 18, 2015

(54) SURGICAL ROBOT AND SURGICAL ROBOT CONTROL METHOD

(71) Applicant: Samsung Electronics Co., Ltd., Suwon-si, Gyeonggi-do (KR)

(72) Inventors: Kyung Won Moon, Yongin-si (KR); Tae Sin Ha, Seongnam-si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 89 days.

(21) Appl. No.: 13/921,340

(22) Filed: Jun. 19, 2013

(65) Prior Publication Data
US 2014/0142592 A1 May 22, 2014

(30) Foreign Application Priority Data

Nov. 22, 2012 (KR) .................. 10-2012-0132922

(51) Int. Cl.
A61B 19/00 (2006.01)

(52) U.S. Cl.
CPC ..... *A61B 19/2203* (2013.01); *A61B 2019/2223* (2013.01); *A61B 2019/2292* (2013.01); *A61B 2019/2296* (2013.01); *Y10S 901/08* (2013.01)

(58) Field of Classification Search
CPC .............. G06F 3/016; G06F 2203/014; G06F 2203/015; G06F 3/0414; G06F 1/266; G06F 2203/013; G06F 3/011; G06F 3/0383; A61B 19/2203; A61B 2019/2223; A61B 2019/2292; A61B 2019/2296; A61B 2019/465; Y10S 901/08; A63F 13/06; A63F 2300/1025; A63F 2300/1031; A63F 2300/1037; G05G 9/047; G05G 2009/04766; G05G 2009/04777; H04L 67/38; H01H 2003/008
See application file for complete search history.

(56) References Cited

U.S. PATENT DOCUMENTS

| | | | | |
|---|---|---|---|---|
| 5,691,898 A * | 11/1997 | Rosenberg et al. | ............. | 700/85 |
| 5,742,278 A * | 4/1998 | Chen et al. | ..................... | 345/156 |
| 5,907,487 A * | 5/1999 | Rosenberg et al. | ............. | 700/85 |
| 6,342,880 B2 * | 1/2002 | Rosenberg et al. | ........... | 345/161 |
| 6,348,911 B1 * | 2/2002 | Rosenberg et al. | ........... | 345/161 |
| 7,778,733 B2 * | 8/2010 | Nowlin et al. | ................ | 700/260 |
| 2005/0200324 A1 | 9/2005 | Guthart et al. | | |
| 2009/0000626 A1 * | 1/2009 | Quaid et al. | .................. | 128/898 |
| 2009/0088775 A1 * | 4/2009 | Swarup et al. | ................ | 606/130 |
| 2011/0015649 A1 * | 1/2011 | Anvari et al. | ................ | 606/130 |
| 2012/0109377 A1 * | 5/2012 | Stern et al. | .................... | 700/259 |

FOREIGN PATENT DOCUMENTS

| | | |
|---|---|---|
| JP | 6-39760 | 2/1994 |
| JP | 8-281573 | 10/1996 |
| JP | 2010-58202 | 3/2010 |

* cited by examiner

*Primary Examiner* — Bao Long T Nguyen
(74) *Attorney, Agent, or Firm* — Harness, Dickey & Pierce, PLC

(57) ABSTRACT

A surgical robot and a surgical robot control method ensure a stable change of an operation mode. The surgical robot includes a master device having an input unit, a slave device having at least one robotic surgical instrument that is remotely controlled by the master device, and a controller that performs a mode change process to gradually vary the strength of a feedback signal fed back from the slave device to the input unit for a predetermined time when a signal for a change of an operation mode is input via the input unit.

14 Claims, 15 Drawing Sheets

SURGICAL ROBOT AND SURGICAL ROBOT CONTROL METHOD

CROSS-REFERENCE TO RELATED APPLICATIONS

This application claims the priority benefit of Korean Patent Application No. 10-2012-0132922, filed on Nov. 22, 2012 in the Korean Intellectual Property Office, the disclosure of which is incorporated herein by reference.

BACKGROUND

1. Field

Embodiments disclosed herein relate to a surgical robot and a surgical robot control method, which ensure a stable operation-mode change of the surgical robot.

2. Description of the Related Art

A robot may be embodied by a mechanical device that automatically performs any operation or work. Robots work using power instead of people or along with people, and may be classified into home robots, exploration robots, industrial robots, and medical robots, for example, according to a field of use thereof.

A medical robot may be referred to as a surgical robot and may be applied to various fields of medicine including surgery. The surgical robot may include a master device and a slave device that may be remotely controlled by the master device.

The master device may include an input unit, and an operator may remotely control movement of the slave device by manipulating the input unit.

The slave device may include a robotic surgical instrument provided with a surgical tool, a robot arm to which the surgical instrument is coupled, and a body to which the robot arm is connected. The robotic surgical instrument may include a plurality of links, and a motor may be provided at each connection portion (i.e. joint) between links. The motor provided at the joint may be driven to track a speed set by the input unit of the master device.

SUMMARY

It is an aspect of the present invention to provide a surgical robot and a surgical robot control method, which ensure stable operation mode change of the surgical robot.

Additional aspects of the invention will be set forth in part in the description which follows and, in part, will be apparent from the description, or may be learned by practice of the invention.

In accordance with one aspect of the invention, a surgical robot includes a master device having an input unit, a slave device having at least one robotic surgical instrument that is remotely controlled by the master device, and a controller that performs a mode change process to gradually vary the strength of a feedback signal fed back from the slave device to the input unit for a predetermined time when a signal for change of an operation mode is input via the input unit.

The operation mode may be any one of a force feedback mode that feeds back force generated in the at least one robotic surgical instrument via interaction with the external environment to the master device, and a non-force feedback mode that does not feed back the force generated in the at least one robotic surgical instrument to the master device.

The controller may gradually decrease the strength of the feedback signal fed back to the input unit for the predetermined time using a decreasing scaling function if the operation mode is changed from a force feedback mode to a non-force feedback mode. An output value of the decreasing scaling function may vary from 1 to 0 for the predetermined time. The decreasing scaling function may be selected by an operator of the surgical robot from among a plurality of pre-stored decreasing scaling functions. The predetermined time may be changeable by an operator of the surgical robot. The predetermined time may vary according to the strength of the feedback signal fed back to the input unit.

The controller may gradually increase the strength of the feedback signal fed back to the input unit for the predetermined time using an increasing scaling function if the operation mode is changed from a non-force feedback mode to a force feedback mode. An output value of the increasing scaling function may vary from 0 to 1 for the predetermined time. The increasing scaling function may be selected by an operator of the surgical robot from among a plurality of pre-stored increasing scaling functions. The predetermined time may be changeable by an operator of the surgical robot. The predetermined time may vary according to the strength of the feedback signal fed back to the input unit. The controller may be included in the master device or in the slave device.

In accordance with another aspect of the invention, a surgical robot control method includes receiving a manipulation instruction input by an operator via an input unit provided in a master device, generating a control signal to control at least one robotic surgical instrument provided in a slave device such that the robotic surgical instrument tracks movement of the input unit, transmitting the control signal to the slave device, and performing a mode change process to gradually vary the strength of a feedback signal fed back from the slave device to the input unit for a predetermined time when an operation mode is changed via the input unit.

The operation mode may include a force feedback mode that feeds back force generated in the at least one robotic surgical instrument via interaction with an external environment to the master device, and a non-force feedback mode that does not feed back the force generated in the at least one robotic surgical instrument to the master device.

Performing the mode change process may include gradually decreasing the strength of the feedback signal fed back to the input unit for a predetermined time using a decreasing scaling function if the operation mode is changed from a force feedback mode to a non-force feedback mode. The predetermined time may vary according to the strength of the feedback signal fed back to the input unit. The decreasing scaling function may be non-linear.

The performing the mode change process may include gradually increasing the strength of the feedback signal fed back to the input unit for a predetermined time using an increasing scaling function if the operation mode is changed from a non-force feedback mode to a force feedback mode. The predetermined time may vary according to the strength of the feedback signal fed back to the input unit. The increasing scaling function may be non-linear.

In accordance with another aspect of the invention, a robot may include a slave device having at least one instrument, a master device to remotely perform an operation using the at least one instrument via the slave device, and a controller to perform a feedback mode change process by temporarily applying a scaling function to a feedback signal fed back from the slave device to the master device, in response to a change in the feedback mode. The controller may temporarily apply the scaling function to the feedback signal for a variable amount of time according to a magnitude of force fed back to the master device, or according to a user input. The robot may further include a storage unit to pre-store scaling functions and setting values associated with the feedback mode change process. The master device may include an input unit to select the feedback mode and to control the instrument provided at the slave device. The input unit may include at least one haptic device to control an operation of the instrument. The master device may further include at least one drive unit to drive the at least one haptic device based on the feedback signal, wherein the at least one haptic device may be driven according to the scaling function applied to the feedback signal.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

The advantages and features of the embodiments of the present invention and the way of attaining them will become apparent with reference to embodiments described below in detail in conjunction with the accompanying drawings. The embodiments of the present invention, however, may be embodied in many different forms and should not be construed as being limited to example embodiments set forth herein. Rather, these example embodiments are provided so that this disclosure will be thorough and complete and will fully convey the scope to those skilled in the art. The scope of the present invention should be defined by the claims and equivalents thereof.

First, an embodiment of a surgical robot will be schematically described with reference to FIG. 1.

Figure 1:
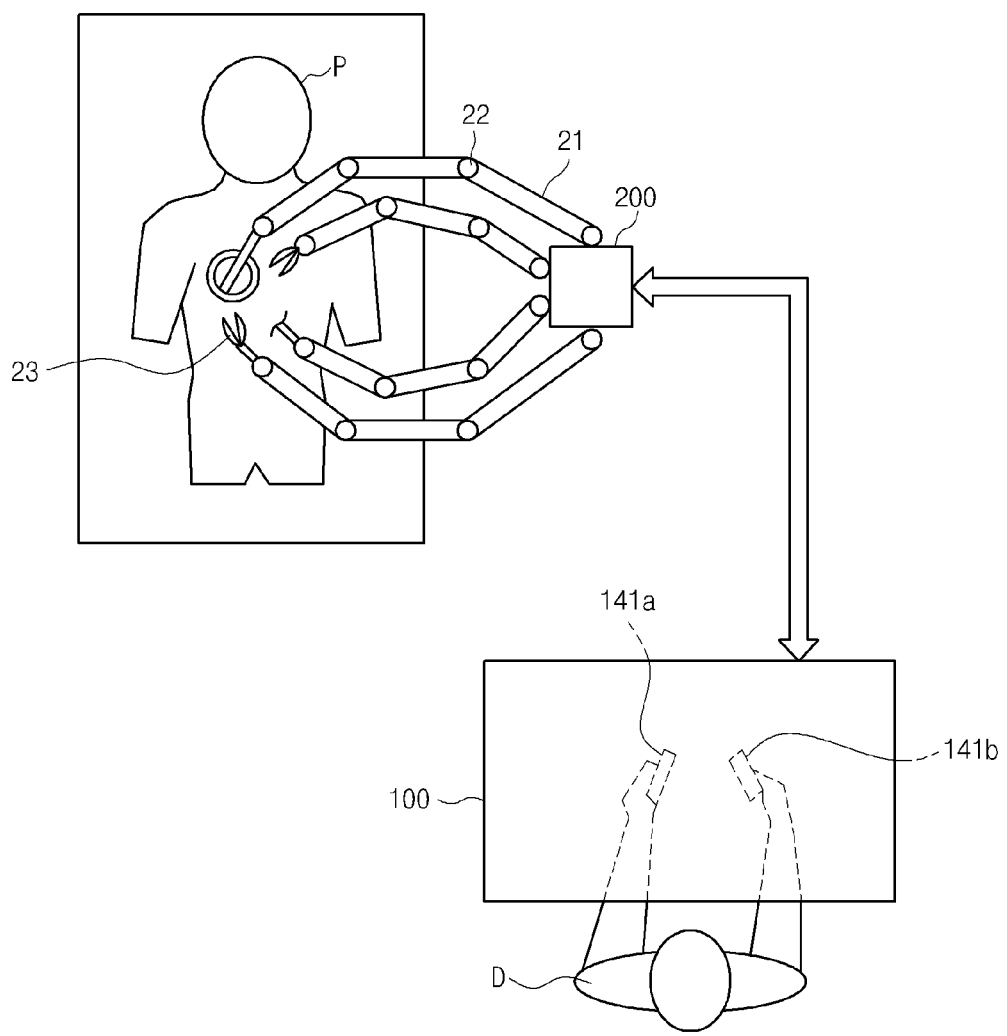
FIG. 1 is a view illustrating an embodiment of a surgical robot.

As illustrated in FIG. 1, the surgical robot may include a master device 100 and a slave device 200.

The master device 100 and the slave device 200 may include the same or similar functional components. In the following description, components included in the master device 100 are designated 'first', and components included in the slave device 200 are designated 'second', to distinguish the components of the master device 100 from the components of the slave device 200. Here, it is noted that the slave device 200 may be positioned in a surgery site as needed to perform a desired operation. For example, the slave device 200 may be portable, may be fixed, or may be detachably disposed to a site (e.g., the railing of an operating table, or other object).

The master device 100 may have a function of controlling the slave device 200. To this end, the master device 100 may include an input unit 140 (see FIG. 6).

The input unit 140 may receive an instruction for selection of an operation mode of the surgical robot, or an instruction for remote control of operations of the slave device 200 input by an operator D. To this end, the input unit 140 may include at least one of a haptic device, a clutch pedal, a switch, and a button. The input unit 140 may include a plurality of buttons, keys, and joysticks. Also, the input unit 140 may include an apparatus or device such as keyboard, pedal or footswitch, mouse, touchscreen, or voice control or microphone, to enable a user to control the surgical robot. The input unit 140 may further have additional features to assist the user in operating the surgical robot, including haptic feedback capability, head-mounted displays, virtual reality devices, or augmented virtual reality devices, for example. In the following description, an input unit 140 including a haptic device will be described by way of example.

Although not illustrated in detail in the drawings, the haptic device may include at least one handle unit. FIG. 1 illustrates the case in which the haptic device includes two handle units 141a and 141b. The operator D may manipulate the handle units 141a and 141b respectively with both hands to control operations of robotic surgical instruments provided at tip ends of robot arms.

Figure 6:
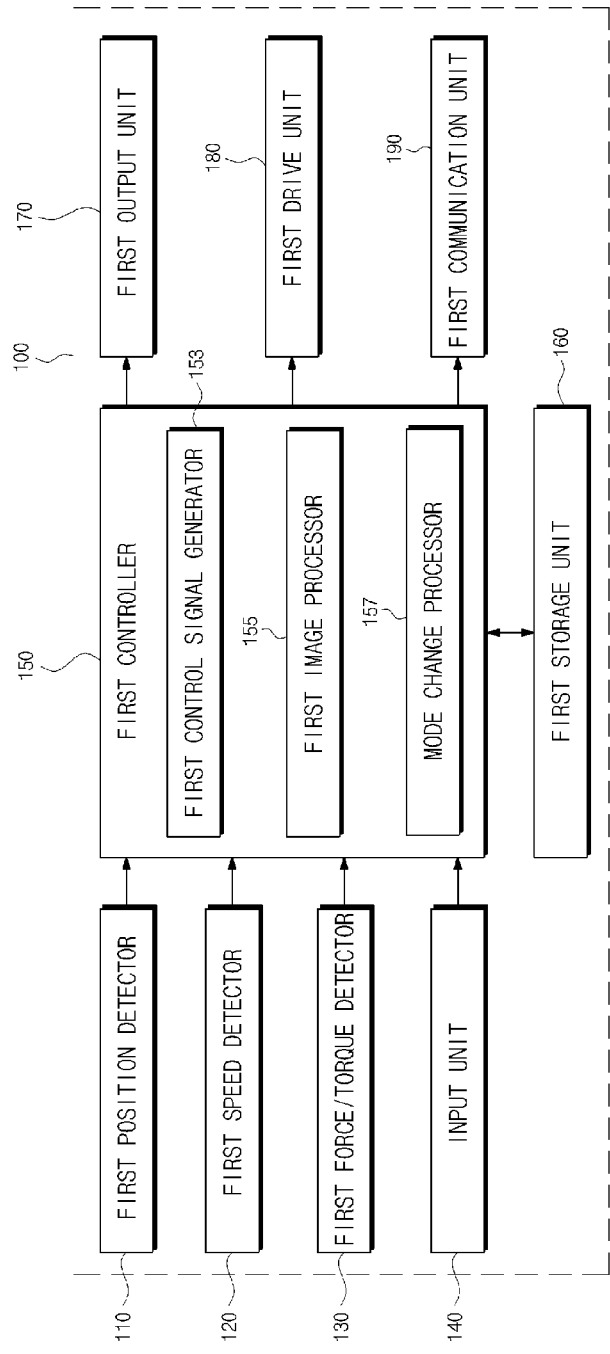
FIG. 6 is a view illustrating an embodiment of a control configuration of a master device.

Although not illustrated in the drawings, each of the handle units 141a and 141b may include a first end-effector, a plurality of first links, a plurality of first joints, and first detectors 110, 120 and 130 (see FIG. 6).

The first end-effector may refer to a component that the hand of the operator D touches. That is, the first end-effector may have a shape or form such that an operator interacting with the first end-effector may control an operation, movement, or function of a surgical instrument disposed at the slave device. For example, the first end-effector may take the form of a pencil or stick to allow the operator D to hold the first end-effector, or may take the form of scissors to allow the operator D to insert at least one finger into the first end-effector. However, the shape of the first end-effector is not limited to the aforementioned examples, and any other shapes are within the scope of the embodiments so long as they are efficient to control operations of the robotic surgical instrument. In addition, the first end-effectors provided respectively at the handle units 141a and 141b may have the same shapes or different shapes.

The first joints refer to connection portions between links. The first joints may have at least 1 degree of freedom. Here, a Degree of Freedom (DOF) refers to a DOF with regard to kinematics or inverse kinematics. The DOF of a instrument refers to the number of independent motions of a instrument, or the number of variables that determine independent motions at relative positions between links. For example, an object in a 3D space defined by X-, Y-, and Z-axes has at least one DOF of 3 DOF to determine a spatial position (a position on each axis) of the object, and 3 DOF to determine a spatial orientation of the object (a rotation angle relative to each axis). More specifically, it will be appreciated that if an object is movable along each of X-, Y- and Z-axes and is rotatable about each of X-, Y- and Z-axes, it will be appreciated that the object has 6 DOF.

The first detectors 110, 120 and 130 may be provided at each first joint to detect data regarding the state of the first joint. To this end, the first detectors 110, 120 and 130 may include a first position detector 110 to detect a position of the first joint, a first speed detector 120 to detect a speed of the first joint, and a first force/torque detector 130 to detect a force/torque applied to the first joint. In this case, the first speed detector 120 may be omitted according to the kind of a position sensor used as the first position detector 110.

As described above, the master device 100 may be connected to the slave device 200 via a network. In this case, the network may be a wired network, a wireless network, or a combination thereof. The master device 100, connected to the slave device 200 via a network, may transmit a control signal to the slave device 200. In addition, the master device 100 may receive a feedback signal, indicating force applied to the robotic surgical instrument, from the slave device 200.

The slave device 200 may be moved according to the control signal received from the master device 100. The slave device 200 may include a body and a plurality of robot arms connected to the body.

Each of the robot arms may include a plurality of links 21 and a plurality of joints 22. The joints 22 of the robot arm serve to connect the links 21 of the robot arm to each other, and may have at least 1 DOF Each joint 22 of the robot arm may be provided with a drive unit (not shown) that is driven according to a control signal of the master device 100. Accordingly, the operator D may control movement of the robot arm using the master device 100. The robot arm may be moved according to a control signal of the master device 100, or may be moved by external force. A robotic surgical instrument may be provided at a distal end of the robot arm. During surgery, the robotic surgical instrument is inserted into the body of an object, for example, a patient P. In this case, the robot arm is located outside of the body of the patient P, and serves to support the robotic surgical instrument inserted into the body of the patient P.

Figure 2:
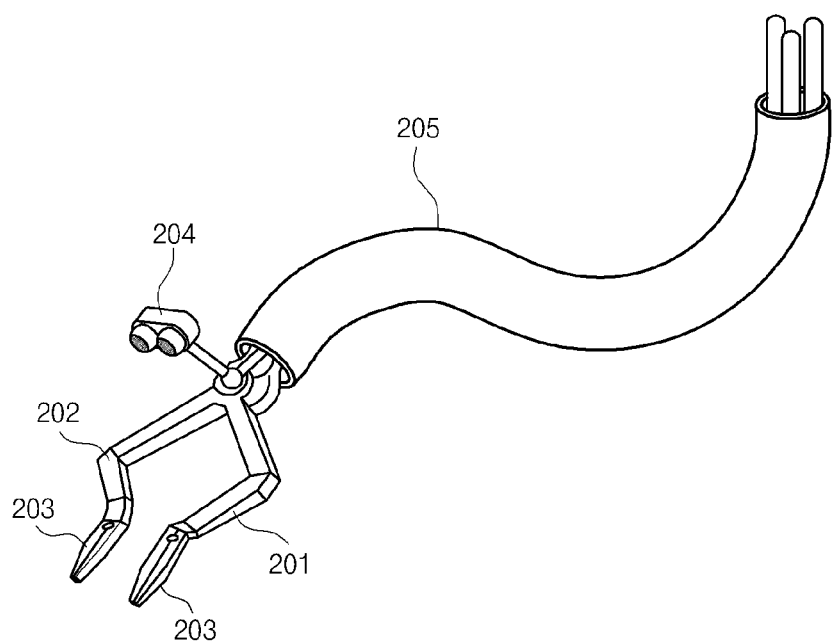
FIG. 2 is a view illustrating a robotic surgical instrument provided at a robot arm of the surgical robot.
Figure 7:
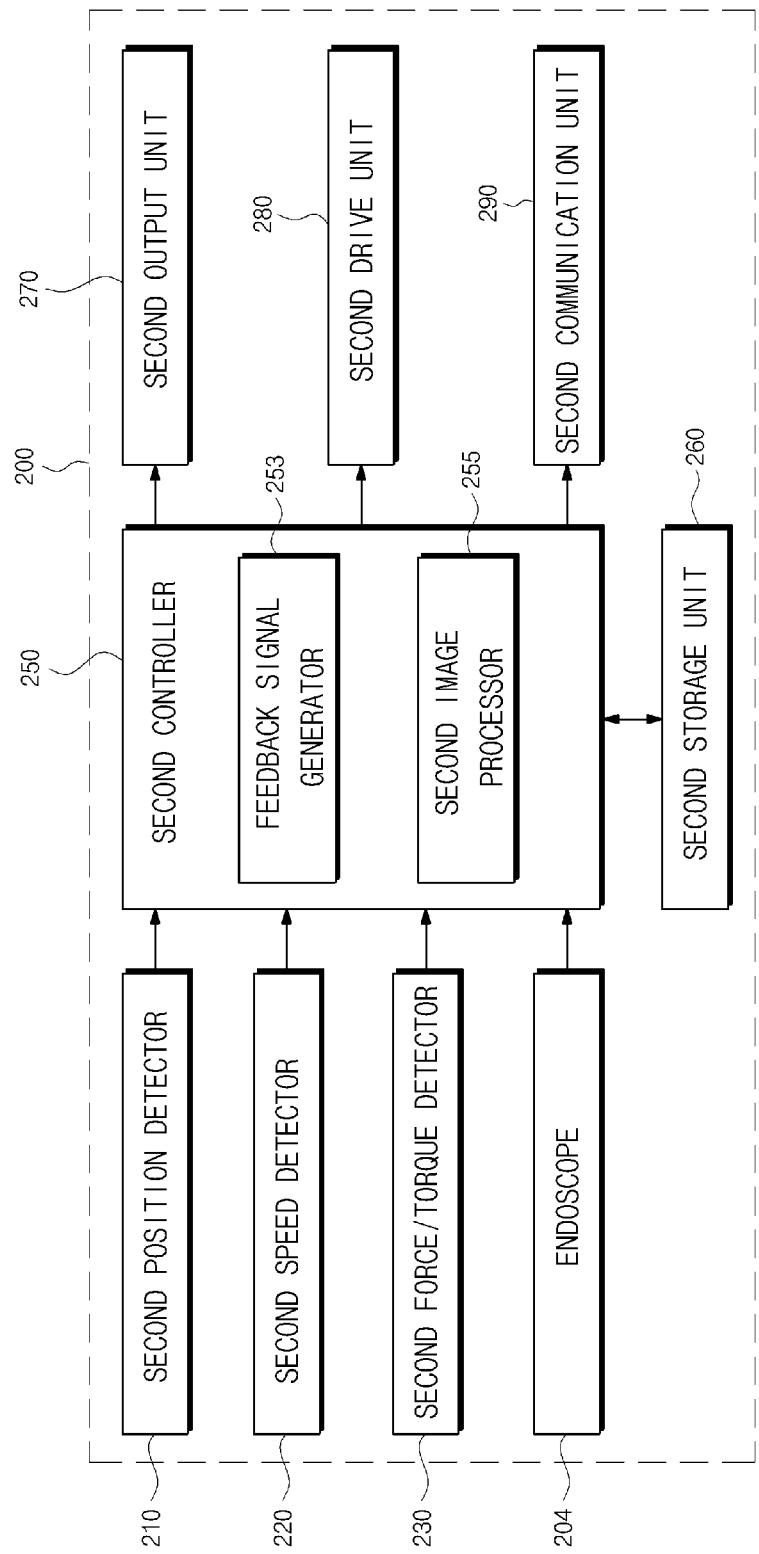
FIG. 7 is a view illustrating an embodiment of a control configuration of a slave device.

Each robotic surgical instrument 23, as illustrated in FIG. 2, may include second end-effectors 203 and 204, a plurality of second links 201, a plurality of second joints 202, and second detectors (see 210, 220, and 230 of FIG. 7).

The second end-effectors 203 and 204 may be provided respectively at distal ends of the links. The second end-effectors 203 and 204 may include an endoscope 204 and a surgical tool 203. The surgical tool 203 may include at least one of tools for resecting, cutting, coagulating, washing, and gripping of bodily tissues. The surgical tool may be, for example, a needle holder, micro-dissector, staple applier, tacker, suction irrigation tool, clip applier, cutting blade, irrigator, catheter, suction orifice, surgical knife, surgical forceps, scissors, a cautery (a tool for burning or cutting a diseased part by using electric energy or heat energy), an endoscope camera, or the like.

Each second joint 202 may be one of a fixed joint, a revolute joint that rotates about a designated one of X-, Y-, and Z-axes, and a prismatic joint that moves along a designated one of X-, Y-, and Z-axes. The second joints 202 may have at least 1 DOF.

Each second joint 202 may be provided with a second drive unit 280. The second drive unit 280 may apply drive power to the second joint 202 according to a control signal received from the master device 100. The second drive unit 280, for example, may be one of a motor, a vacuum pump, and a hydraulic pump. In the following description, a motor as the second drive unit 280 will be described by way of example.

The second detectors 210, 220 and 230 may be provided at each second joint 202 to detect data regarding the state of the second joint 202. To this end, the second detectors 210, 220 and 230 may include a second position detector 210 to detect a position of the second joint 202, a second speed detector 220 to detect a speed of the second joint 202, and a second force/torque detector 230 to detect a force/torque applied to the second joint 202. In this case, the second speed detector 220 may be omitted according to the kind of a position sensor used as the second position detector 210.

The above-described surgical robot may be a multi-port system, or may be a single-port system. In the multi-port system, the plurality of robotic surgical instruments 23 is introduced into the visceral cavity of the patient P through individual invasive regions. In the single-port system, the plurality of robotic surgical instruments 23 is introduced into the visceral cavity of the patient P through a single invasive region.

FIG. 2 illustrates a single-port system. As illustrated in FIG. 2, in the single-port system, a guide tube 205 may be used to introduce the plurality of robotic surgical instruments 23 into the visceral cavity of the patient P.

Movement of the guide tube 205 may be actively controlled using an actuator. Thus, the guide tube 205 is first introduced into the visceral cavity of the patient P, and thereafter is fixed so as not to move. Then, as the robotic surgical instruments 23 are inserted into the guide tube 205 and moved along an inner wall of the guide tube 205, the second end-effectors 203 and 204 may reach a target region.

In addition, after the robotic surgical instruments 23 are inserted into the guide tube 205, the guide tube 205 may be introduced into the visceral cavity of the patient P. In this case, once the guide tube 205 reaches a target region, the guide tube 205 is fixed stationary, and the second end-effectors, i.e. the surgical tool 203 and the endoscope 204 of the robotic surgical instruments 23 inserted into the guide tube 205 may be discharged from the guide tube 205. The endoscope 204 discharged from the guide tube 205 may function to capture an image of a surgical region, and the surgical tool 203 discharged from the guide tube 205 may function to pick up or resect (e.g., remove) bodily tissues.

The surgical robot as described above may provide a variety of operation modes. The operation modes of the surgical robot may be classified into a force feedback mode and a non-force feedback mode, for example.

The force feedback mode refers to a mode that feeds back force generated in the slave device 200 to the master device 100. One example of the force feedback mode may be a surgical tool manipulation mode. The surgical tool manipulation mode refers to a state in which the surgical tool 203 provided at the robot arm may be manipulated using the haptic device provided at the master device 100. If force is generated in the surgical tool 203 via interaction with the external environment during execution of the force feedback mode, the force generated in the surgical tool 203 may be fed back to the input unit 140 of the master device 100, for example, to the haptic device. As such, the operator D may perceive the force generated in the surgical tool 203 via the input unit 140.

The non-force feedback mode refers to a mode that does not feed back force generated in the slave device 200 to the master device 100. One example of the non-force feedback mode may be an endoscope manipulation mode to manipulate operations of the endoscope 204. If the surgical robot is the single-port system as illustrated in FIG. 2, a guide tube manipulation mode to manipulate operations of the guide tube 205 may be included in the non-force feedback mode.

Selection of an operation mode of the surgical robot may be accomplished via the input unit 140 of the master device 100. In one example, a button or switch for selection of an operation mode, such as the surgical tool manipulation mode, the endoscope manipulation mode, the guide tube manipulation mode, or the like, may be provided at the haptic device as the input unit 140, and an operation mode corresponding to the button or switch selected by the operator D may be executed. In another example, if the operator D pushes at least one clutch pedal among a plurality of clutch pedals provided at the bottom of the master device 100, a previous operation mode may be inactivated and an operation mode associated with the clutch pedal may be activated.

Operation mode changes of the surgical robot may occur before or after surgery is initiated. In particular, it may be necessary to pay particular attention to change of an operation mode during surgery. This is because when an operation mode of the surgical robot is changed, the magnitude of force fed back to the handle units 141a and 141b of the master device 100 suddenly varies, which may cause unintentional movement of the handle units 141a and 141b. A more detailed description thereof will follow with reference to FIG. 3.

Figure 3:
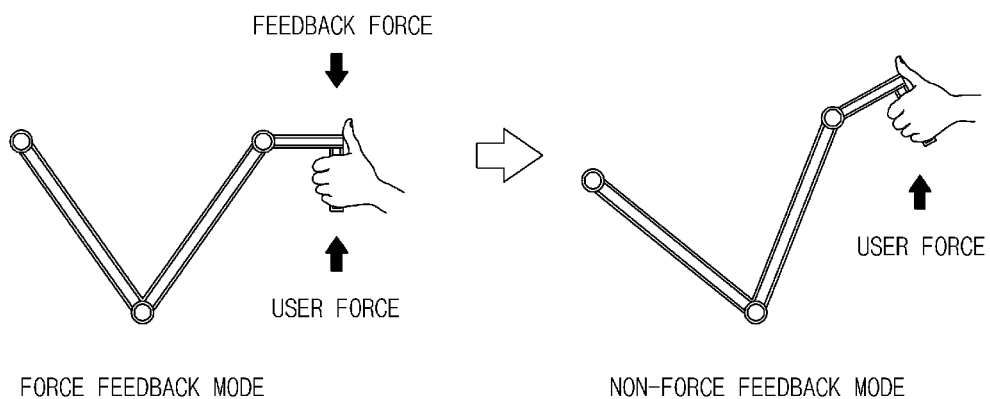
FIG. 3 is a view explaining a situation that may occur at a handle unit of a master device when an operation mode of the surgical robot is changed from a force feedback mode to a non-force feedback mode.

FIG. 3 is a view explaining a situation that may occur at the handle units 141a and 141b of the master device 100 when an operation mode of the surgical robot is changed from a force feedback mode to a non-force feedback mode.

For convenience of description, it is assumed that the surgical tool 203 provided at the robotic surgical instrument 23 picks up an organ of the patient P. In this case, force is applied to the surgical tool 203 in the direction of gravity by the weight of the organ. The force applied to the surgical tool 203 may be fed back to the handle units 141a and 141b of the master device 100. As a result, the operator D may indirectly perceive the force applied to the surgical tool 203 via the handle units 141a and 141b, and may apply force opposite to the feedback force to the handle units 141a and 141b (see the left drawing of FIG. 3). Then, the master device 100 may generate a control signal based on the force applied to the handle units 141a and 141b by the operator D, and may transmit the generated control signal to the slave device 200. Thereafter, the robotic surgical instrument 23 of the slave device 200 may be operated according to the control signal received from the master device 100 and may maintain a pickup posture without a risk of falling of the organ from the surgical tool 203.

If it is necessary to adjust a position of the endoscope 204 in the execution state of the force feedback mode, a situation in which the operator D selects the endoscope manipulation mode may be assumed. However, since the endoscope manipulation mode is a non-force feedback mode, force feedback to the handle units 141a and 141b of the master device 100 stops when the endoscope manipulation mode is selected. Through this sudden force feedback stop, force fed back to the handle units 141a and 141b disappears, which may cause the handle units 141a and 141b to be suddenly moved upward by force that the user has applied to the handle units 141a and 141b in the force feedback mode (see the right drawing of FIG. 3). This unintentional movement of the handle units 141a and 141b due to operation mode change may be dangerous to the patient P.

Accordingly, when changing an operation mode of the surgical robot, it may be necessary to gradually change the magnitude of force fed back to the handle units 141a and 141b of the master device 100. In the following description, an operation of gradually varying the magnitude of force fed back to the handle units 141a and 141b upon change of an operation mode is referred to as a 'mode change process'.

A scaling function may be used for the mode change process. An appropriate scaling function may be selected according to whether an operation mode of the surgical robot is changed from a force feedback mode to a non-force feedback mode or from a non-force feedback mode to a force feedback mode.

First, the case in which an operation mode of the surgical robot is changed from a force feedback mode to a non-force feedback mode will be described. In this case, a mode change process to successively decrease force fed back to the handle units 141a and 141b may be performed. To this end, a decreasing scaling function, an output value of which varies from 1 to 0 for a predetermined time may be used.

Figure 4A:
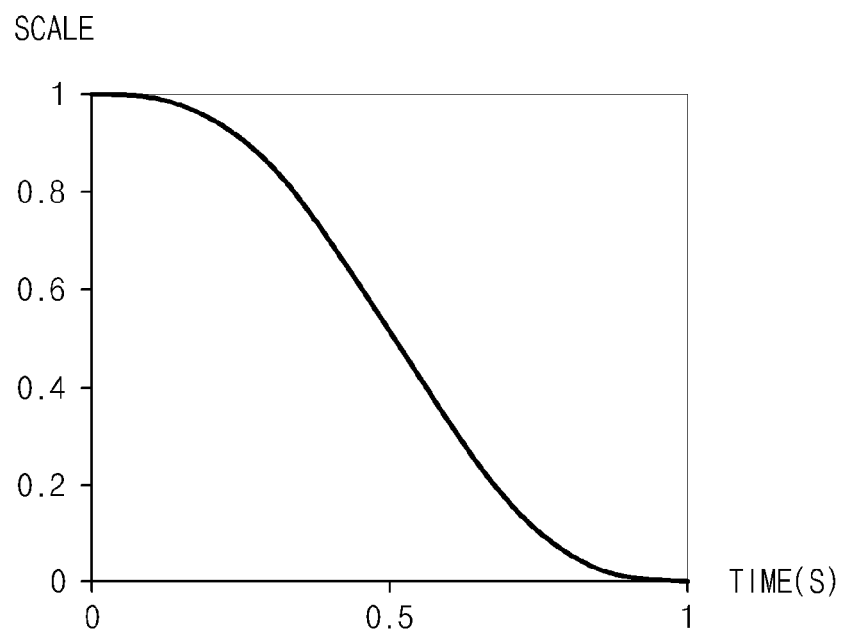
FIG. 4A is a view illustrating one example of a decreasing scaling function.

FIG. 4A is a view illustrating one example of a decreasing scaling function. In the graph of FIG. 4A, the abscissa represents time and the ordinate represents an output value. It will be appreciated that an output value of the decreasing scaling function illustrated in FIG. 4A varies from 1 to 0 as time varies from 0 sec to 1 sec. It will further be appreciated that the output value of the decreasing scaling function decreases in a non-linear manner. One example of the scaling function may include a minimum jerk function. The minimum jerk function may be represented by the following Equation 1.

$$\text{result} = x_i + (x_f - x_i) \times (10 \cdot t_d^3 - 15 \cdot t_d^4 + 6 \cdot t_d^5), \ t_d = t_c/t_t \qquad \text{Equation 1}$$

In Equation 1, $t_c$ denotes current time, $t_t$ denotes total time, $x_i$ denotes an initial output value, and $x_f$ denotes a final output value. $t_c$ is a value varying from 0 to $t_t$. $t_d$ may be calculated by dividing $t_c$ by $t_t$. In addition, $t_t$ is a fixed value and may be previously designated. In the graph illustrated in FIG. 4A, it will be appreciated that $x_i$ is 1, $x_f$ is 0, and $t_t$ is 1 sec.

Here, a value of $t_t$ is not limited to 1 and may be set to other values. In one example, a value of $t_t$ may be changed by the operator D. That is, a value of $t_t$ may be set according to the preferences of the operator D. In this case, a value of $t_t$ may be set before surgery.

In another example, a value of $t_t$ may vary according to the strength of a signal fed back from the slave device 200. More specifically, the greater the magnitude of force generated in the surgical tool 203, the greater the value of $t_t$.

In a further example, the magnitude of force that may be generated in the robotic surgical instrument 23 may be divided into a plurality of ranges, and a value of $t_t$ may be differently set on a per range basis. In addition, a real range of the magnitude of force generated in the surgical tool 203 is judged and a value of $t_t$ corresponding to the judged range is selected, such that a mode change process may be performed according to a selected value of $t_t$.

Figure 4B:
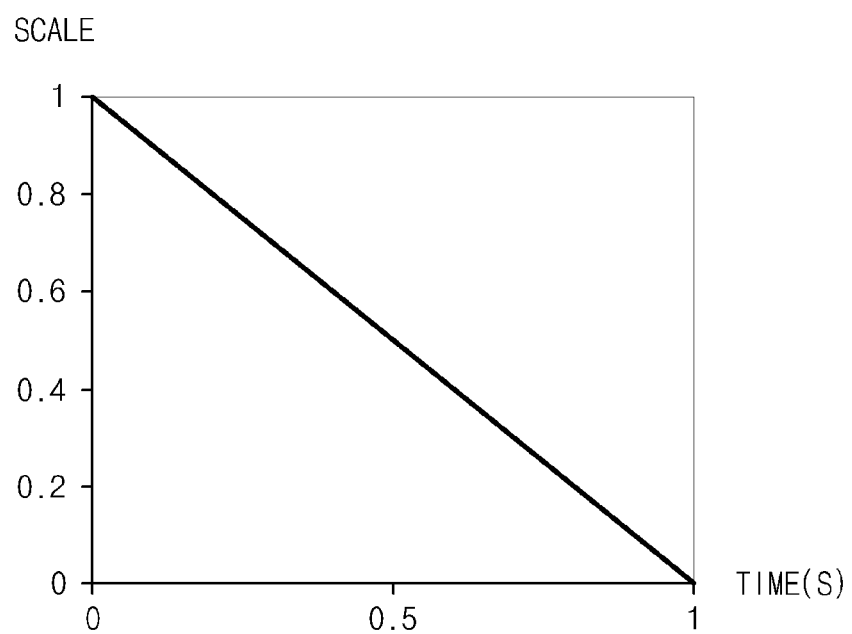
FIG. 4B is a view illustrating another example of a decreasing scaling function.

FIG. 4B is a view illustrating another example of a decreasing scaling function. It will be appreciated that an output value of the decreasing scaling function illustrated in FIG. 4 linearly varies from 1 to 0 as time varies from 0 sec to 1 sec.

Figure 4C:
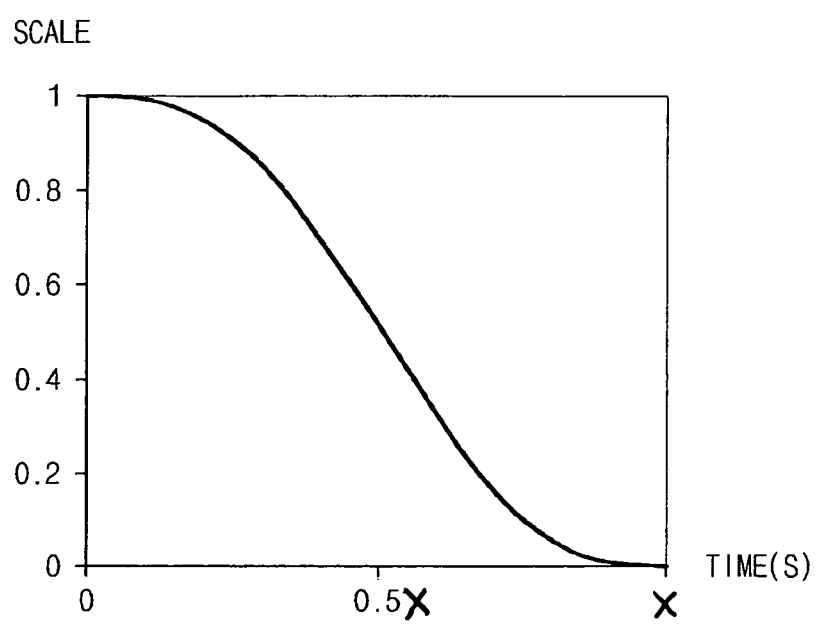
FIG. 4C is a view illustrating yet another example of decreasing scaling Function.
Figure 4D:
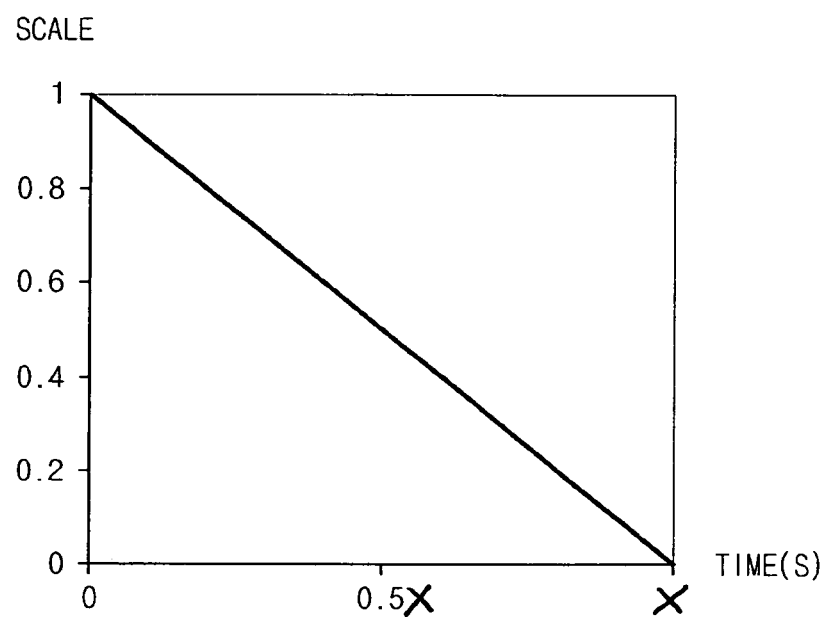
FIG. 4D is a view illustrating still another example of a decreasing scaling function.

In addition to the decreasing scaling functions illustrated in FIGS. 4A and 4B, any other functions are within the scope of the embodiments so long as they are functions, an output value of which varies from 1 to 0 for a predetermined time. For example, FIGS. 4C and 4D are similar to FIGS. 4A and 4B, except that the value X (in seconds) of $t_t$ is variable according to the strength of a signal fed back from the slave device 200.

Next, the case in which an operation mode of the surgical robot is changed from a non-force feedback mode to a force feedback mode will be described. In this case, a mode change process to successively increase force fed back to the handle units 141*a* and 141*b* may be performed. To this end, an increasing scaling function to output a value from 0 to 1 for a predetermined time may be used.

Figure 5A:
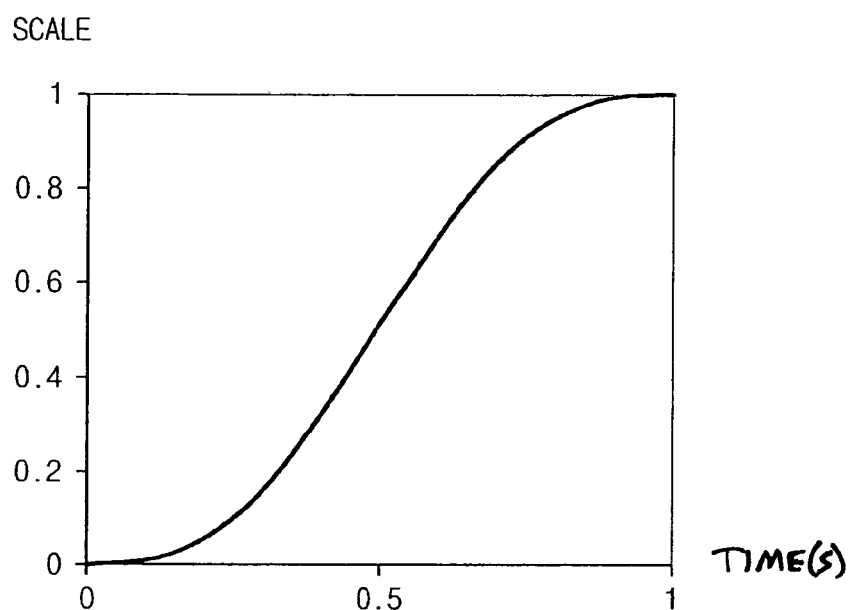
FIG. 5A is a view illustrating one example of an increasing scaling function.

FIG. 5A is a view illustrating one example of an increasing scaling function. It will be appreciated that an output value of the increasing scaling function illustrated in FIG. 5A varies from 0 to 1 as time varies from 0 sec to 1 sec. It will further be appreciated that the output value of the increasing scaling function increases in a non-linear manner.

Figure 5B:
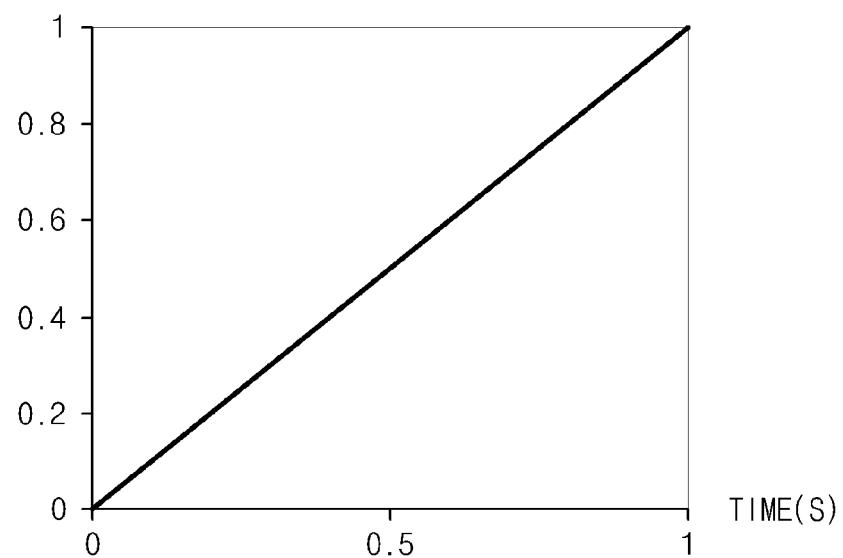
FIG. 5B is a view illustrating another example of an increasing scaling function.

FIG. 5B is a view illustrating another example of an increasing scaling function. It will be appreciated that an output value of the increasing scaling function illustrated in FIG. 5B linearly varies from 0 to 1 as time varies from 0 sec to 1 sec.

Figure 5C:
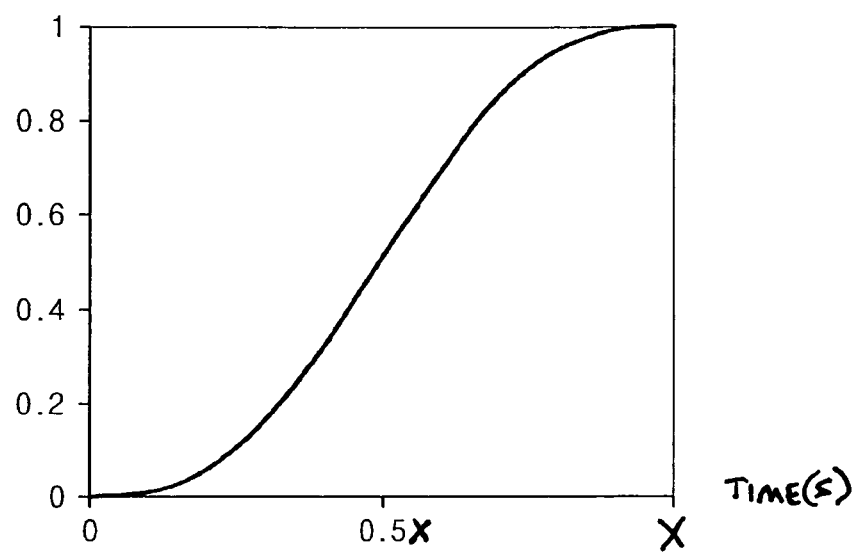
FIG. 5C is a view illustrating yet another example of an increasing scaling function.
Figure 5D:
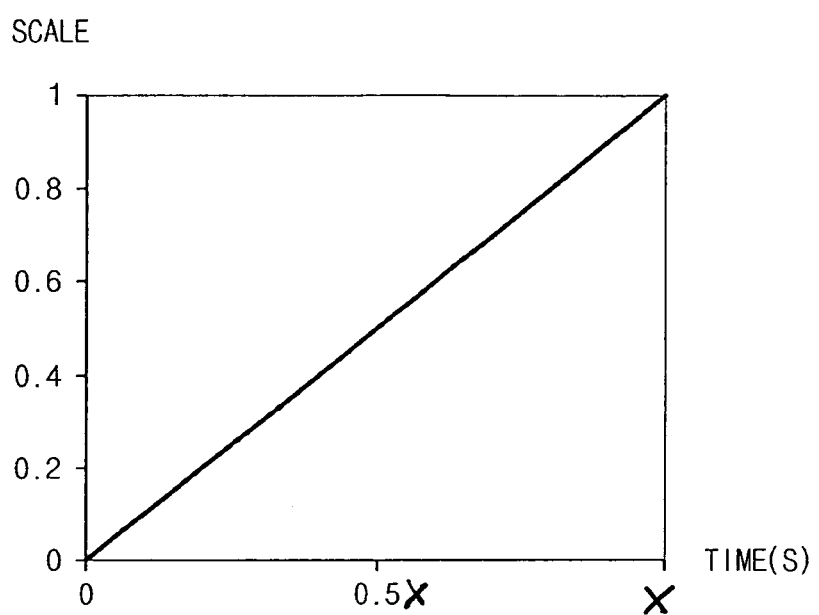
FIG. 5D is a view illustrating still another example of an increasing scaling function.

In addition to the increasing scaling functions illustrated in FIGS. 5A and 5B, any other functions may be within the scope of the embodiments so long as they are functions, an output value of which varies from 0 to 1 for a predetermined time For example, FIGS. 5C and 5D are similar to FIGS. 5A and 5B, except that the value of X (in seconds) of $t_t$ is variable according to the strength of a signal fed back from the slave device 200.

Which one of the above-described decreasing scaling functions or the above-described increasing scaling functions will be used may be preset upon fabrication of the surgical robot. The above-described decreasing scaling functions and/or the above-described increasing scaling functions may be stored in a storage unit. The preset value may be variable or invariable by the operator D.

In the mode change process, a control signal to be transmitted to the handle units 141*a* and 141*b* of the master device 100 may be generated by multiplying a value of force fed back to the handle units 141*a* and 141*b* by an output value of the scaling function. In this case, the control signal to be transmitted to the handle units 141*a* and 141*b* may be generated by the master device 100, or may be generated by the slave device 200. In the following description, the case in which the control signal to be transmitted to the handle units 141*a* and 141*b* is generated by the master device 100 will be described by way of example.

FIG. 6 is a view illustrating an embodiment of a control configuration of the master device 100.

As illustrated in FIG. 6, the master device 100 may include the input unit 140, the first detectors 110, 120 and 130, a first controller 150, a first storage unit 160, a first output unit 170, a first drive unit 180, and a first communication unit 190.

The operator D may input an instruction for selection an operation mode of the surgical robot or an instruction for remote control of operations of the robot arm and/or the robotic surgical instrument 23 using the input unit 140. The input unit 140 may include at least one of a haptic device, a clutch pedal, a switch, and a button. The haptic device may include the handle units 141*a* and 141*b*. Each of the handle units 141*a* and 141*b* may include the plurality of first links, the plurality of first joints, and the first end-effector.

The first detectors 110, 120 and 130 may be provided at each first joint to detect data regarding the state of the first joint. To this end, the first detectors 110, 120 and 130 may include the first position detector 110, the first speed detector 120, and the first force/torque detector 130.

The first position detector 110 may detect a position (rotation angle) of the first joint. The first position detector 110 may serve as a position sensor. The position sensor, for example, may be a potentiometer or an encoder.

The first speed detector 120 may detect a speed of the first joint. The first speed detector 120 may be omitted according to the kind of a position sensor used as the first position detector 110. If the first speed detector 120 is omitted, a speed signal for the first joint may be acquired using differentiation of a position signal detected by the first position detector 110.

The first force/torque detector 130 may detect a force/torque applied to the first joint. The first force/torque detector 130 may be a force/torque sensor.

The first controller 150 may connect and control components of the master device 100. More specifically, the first controller 150 may generate a control signal required to control the surgical robot. For example, the first controller 150 may generate a control signal to be transmitted to the robotic surgical instruments 23 or a control signal to be transmitted to the handle units 141*a* and 141*b*. The first controller 150 may perform image processing on image data captured by the endoscope 204. In addition, the first controller 150 may perform a mode change process to stably change an operation mode of the surgical robot. To perform the aforementioned operations, the first controller 150 may include a first control signal generator 153, a first image processor 155, and a mode change processor 157.

The first control signal generator 153 may generate a control signal to be transmitted to the robotic surgical instruments 23 of the slave device 200 based on detection signals from the first detectors 110, 120 and 130. The generated control signal may refer to torque values to drive (move or rotate) the robotic surgical instruments 23 such that robotic surgical instruments 23 track movements of the handle units 141*a* and 141*b*.

If a force feedback mode is being executed, the first control signal generator 153 may transmit a feedback signal fed back from each of the robotic surgical instruments 23 to the first drive unit 180. The first drive unit 180 may drive the handle units 141*a* and 141*b* according to the feedback signal. As a result, the operator D may indirectly perceive interaction between the robotic surgical instruments 23 and the external environment.

If the first image processor 155 receives image data from the slave device 200, the first image processor 155 may perform image processing on the received image data. In this case, the received image data may be raw data captured by the endoscope 204, or may be image data primarily processed by the slave device 200. Examples of image processing performed by the first image processor 155 may include expansion, reduction, movement and rotation of an image, generation of a composite of images, and image filtering. The first image processor 155 may perform at least one of the above enumerated image processing operations. However, image processing is not essentially performed and may be omitted as the occasion demands.

The mode change processor 157 may judge whether or not an operation mode of the surgical robot is changed based on an instruction input via the input unit 140. If the judged result shows that the operation mode is changed, a mode change process for stable change of the operation mode may be performed. As described above, the mode change process serves to gradually vary the magnitude of force fed back to the handle units 141*a* and 141*b* of the master device 100 for a predetermined time. Here, the predetermined time may refer to an overall implementation time of the mode change process. This time may be set to a fixed value. Alternatively, the time may be variably set by the operator D before surgery according to the kind of surgery or the preferences of the operator D. Alternatively, the time may be variable in proportion to the magnitude of force fed back to the handle units 141*a* and 141*b*. For example, the time may increase when the magnitude of force fed back increases.

When performing the mode change process, a comparison between a previous operation mode and a current operation mode may be performed to find an optimal mode change process.

For example, in the case of change from a force feedback mode to a non-force feedback mode, the mode change processor 157 may generate a control signal to be transmitted to the handle units 141a and 141b by multiplying a value of force fed back to the handle units 141a and 141b by an output value of the above-described decreasing scaling function. The generated control signal may be transmitted to the handle units 141a and 141b, and the handle units 141a and 141b may be driven according to the control signal. By gradually decreasing the magnitude of force fed back to the handle units 141a and 141b for a predetermined time, the operator D may be ready for termination of the force feedback mode. Accordingly, it may be possible to prevent an unintentional movement of the handle units 141a and 141b.

On the other hand, in the case of change from a non-force feedback mode to a force feedback mode, the mode change processor 157 may generate a control signal to be transmitted to the handle units 141a and 141b by multiplying a value of force fed back to the handle units 141a and 141b by an output value of the above-described increasing scaling function. The generated control signal may be transmitted to the handle units 141a and 141b, and the handle units 141a and 141b may be driven according to the control signal. By gradually increasing the magnitude of force fed back to the handle units 141a and 141b for a predetermined time, the operator D may be ready for initiation of the force feedback mode. Accordingly, it may be possible to prevent an unintentional movement of the handle units 141a and 141b.

The first storage unit 160 may store data, algorithms, setting values, etc. required to control the slave device 200. Additionally, the first storage unit 160 may store data, algorithms, setting values, etc. required to perform a mode change process. For example, the first storage unit 160 may store scaling functions and various setting values associated with the respective functions. The first storage unit 160 may also temporarily store, for example, a feedback signal or image data received from the slave device 200.

The first storage unit 160 may be a storage medium, such as a nonvolatile memory device, such as a Read Only Memory (ROM), Programmable Read Only Memory (PROM), Erasable Programmable Read Only Memory (EPROM), and flash memory, a volatile memory device such as a Random Access Memory (RAM), a hard disc, and an optical disc, or combinations thereof. However, examples of the storage unit are not limited to the above description, and the first storage unit may be realized by other various devices and structures as would be understood by those skilled in the art.

The first output unit 170 may output at least one of image data, surgical data, and alarms. To this end, the first output unit 170 may include a first image output unit and a first audio output unit. The first image output unit may output image data or surgical data processed by the first image processor 155. The first audio output unit may output various warning sounds or alarms associated with operations of the surgical robot. In addition, the first output unit 170 may further include a warning lamp to output various warning signs associated with operations of the surgical robot. Further, alarms may be output to a user via a vibration or other physical indicator to warn the user. The first image output unit may be embodied by, for example, a Liquid Crystal Display (LCD), LED display, OLED display, and the like. The first output unit 170 may include speakers and/or a microphone, for example.

The first drive unit 180 may be provided at each first joint of the handle units 141a and 141b. The first drive unit 180 may be driven according to a feedback signal received from the slave device 200 to move or rotate the first joint.

The first communication unit 190 is operated in cooperation with a second communication unit 290 of the slave device 200, and may transmit a control signal to the slave device 200 or may receive image data from the slave device 200. The first communication unit 190 may include a network interface and/or a transceiver, and the like, for example.

FIG. 7 is a view illustrating an embodiment of a control configuration of the slave device 200.

As illustrated in FIG. 7, the slave device 200 may include the endoscope 204, the second detectors 210, 220, and 230, a second controller 250, a second storage unit 260, a second output unit 270, a second drive unit 280, and a second communication unit 290.

The endoscope 204 may capture an image inside the visceral cavity of the patient P or other object. The image captured by the endoscope 204 may be transmitted to the second controller 250 so as to be subjected to image processing, or may be transmitted to the master device 100 through the second communication unit 290.

The second detectors 210, 220 and 230 may be provided at each second joint 202 of the robotic surgical instrument 23 to detect data regarding the state of the second joint 202. To this end, the second detectors 210, 220 and 230 may include a second position detector 210, a second speed detector 220, and a second force/torque detector 230.

The second position detector 210 may detect a position (rotation angle) of the second joint 202 provided at the robotic surgical instrument 23. The second position detector 210 may be a position sensor. Examples of the position sensor may include a potentiometer and an encoder.

The second speed detector 220 may detect a speed of the second joint. The second speed detector 220 may be omitted according to the kind of a position sensor used as the second position detector 210. If the second speed detector 220 is omitted, a speed signal for the second joint may be acquired via differentiation of a position signal detected by the second position detector 210.

The second force/torque detector 230 may detect a force/torque applied to the second joint 202. The second force/torque detector 230 may be a force/torque sensor.

The second controller 250 may connect and control components of the slave device 200. More specifically, the second controller 250 may transmit a control signal transmitted from the master device 100 to the second drive unit 280 so as to drive the robotic surgical instrument 23. If a force feedback mode is being executed, the second controller 250 may generate a feedback signal containing data detected by the detectors 210, 220 and 230 and transmit the feedback signal to the master device 100. In addition, the second controller 250 may perform image processing on image data captured by the endoscope 204. To this end, the second controller 250 may include a feedback signal generator 253 and a second image processor 255.

If movement of the robotic surgical instrument 23 occurs due to interaction with the external environment, the feedback signal generator 253 may generate a feedback signal to be transmitted to the master device 100 based on data detected by the second detectors 210, 220 and 230. The generated feedback signal may refer to a torque value to drive (move or rotate) the handle units 141a and 141b such that the handle units 141a and 141b track movement of the robotic surgical instrument 23.

The second image processor 255 may perform image processing on image data captured by the endoscope 204. Examples of image processing performed by the second image processor 255 may include expansion, reduction, movement and rotation of an image, generation of a composite of images, and image filtering. The second image processor 255 may perform at least one of the above enumerated image processing. The image processing may be omitted as occasion demands. Raw data before image processing or image processed data may be output via the second output unit 270 or may be transmitted to the master device 100.

The second storage unit 260 may store, for example, data or algorithms required to generate a feedback signal, or data or algorithms required to perform image processing. In addition, the second storage unit 260 may temporarily store a control signal received from the master device 100. The second storage unit 260 may be any one of a nonvolatile memory device, a volatile memory device, other various storage media, or a combination thereof. For example, the second storage unit 260 may be a storage medium, such as a nonvolatile memory device, such as a Read Only Memory (ROM), Programmable Read Only Memory (PROM), Erasable Programmable Read Only Memory (EPROM), and flash memory, a volatile memory device such as a Random Access Memory (RAM), a hard disc, and an optical disc, or combinations thereof. However, examples of the storage unit are not limited to the above description, and the second storage unit may be realized by other various devices and structures as would be understood by those skilled in the art.

The second drive unit 280 may be provided at each second joint 202 of the robotic surgical instrument 23. The second drive unit 280 may be driven according to a control signal received from the master device 100 to move or rotate the second joint 202.

The second output unit 270 may include a second image output unit and a second audio output unit. The second image output unit may output image data captured by the endoscope 204, or image data processed by the second image processor 255. The second image output unit, for example, may be a Liquid Crystal Display (LCD), LED display, OLED display, and the like. The second output unit 270 may include speakers and/or a microphone, for example. The second audio output unit may output various warning sounds associated with operations of the surgical robot.

The second drive unit 280 may be driven according to a control signal received from the master device 100 to move or rotate the second joint. Thereby, the robotic surgical tool 23 may be moved to track movement of the handle units 141a and 141b.

The second communication unit 290 may be operated in cooperation with the first communication unit 190 of the master device 100, and may receive a control signal to drive the robotic surgical instrument 23 from the master device 100. The second communication unit 290 may transmit a feedback signal containing data detected by the second detectors 210, 220 and 230 to the master device 100. The second communication unit 290 may include a network interface and/or a transceiver, and the like, for example.

Figure 8:
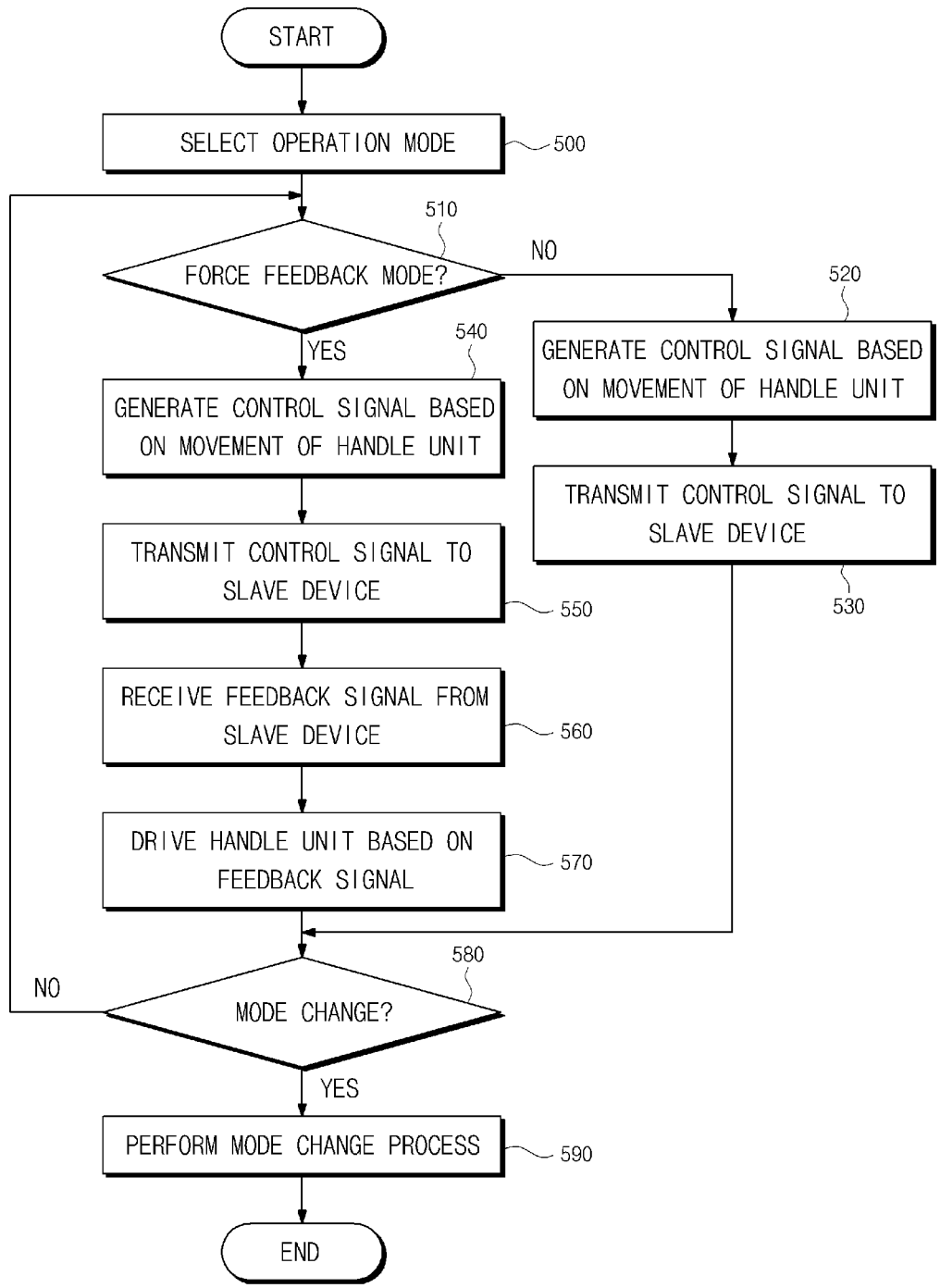
FIG. 8 is a flowchart illustrating an embodiment of a surgical robot control method.

FIG. 8 is a flowchart of an embodiment of a surgical robot control method, which is performed by the master device 100.

First, an operation mode of the surgical robot may be selected (500), and whether or not the selected operation mode is a force feedback mode may be judged or determined (510).

If the judged result shows that the selected operation mode is a non-force feedback mode (No in Operation 510), a control signal to control movement of the surgical tool or instrument (for example, the endoscope 204 or surgical tool 203), or the guide tube 205 which may contain one or more surgical tools or instruments, may be generated based on movement of the handle units 141a and 141b (520). The generated control signal may be transmitted to the slave device 200 (530).

If the judged result shows that the selected operation mode is a force feedback mode (Yes in Operation 510), a control signal to control movement of the surgical tool or instrument (for example, the endoscope 204 or surgical tool 203), or the guide tube 205 which may contain one or more surgical tools or instruments, may be generated based on movement of the handle units 141a and 141b (540). The generated control signal may be transmitted to the slave device 200 (550).

Thereafter, a feedback signal from the slave device 200 may be received (560). The feedback signal may be a control signal generated by the slave device 200 when force is generated in the robotic surgical instrument 23 via interaction between the external environment and the robotic surgical instrument 23, and may contain data detected by the second detectors 210, 220 and 230 of the robotic surgical instrument 23.

Once the feedback signal from the slave device 200 is received, the handle units 141a and 141b may be driven based on the received feedback signal (570). More specifically, the feedback signal received from the slave device 200 may be transmitted to the first drive unit 180, and the first drive unit 180 may drive the handle units 141a and 141b based on the feedback signal. As a result, the operator D may indirectly perceive interaction between the robotic surgical tool 23 and the external environment via the handle units 141a and 141b.

Thereafter, it may be judged whether or not an operation mode of the surgical robot is changed (580). The judgment or determination may be performed by the mode change processor 157. More specifically, the mode change processor 157 may judge whether or not operation mode change occurs by monitoring an instruction input through the input unit 140. For example, operation mode change may be judged by monitoring whether a particular switch or button provided at the handle units 141a and 141b is selected, or whether a clutch pedal is pushed, or whether a voice command is received, for example.

If the judged result shows that the operation mode change does not occur (No in Operation 580), Operations 510 to 570 may be repeated.

If the judged result shows that an operation mode change occurs (Yes in Operation 580), a mode change process to gradually vary the magnitude of force fed back to the handle units 141a and 141b may be executed (590). The mode change process may use a scaling function. Here, Operation 590 will be described in more detail with reference to FIG. 9.

Figure 9:
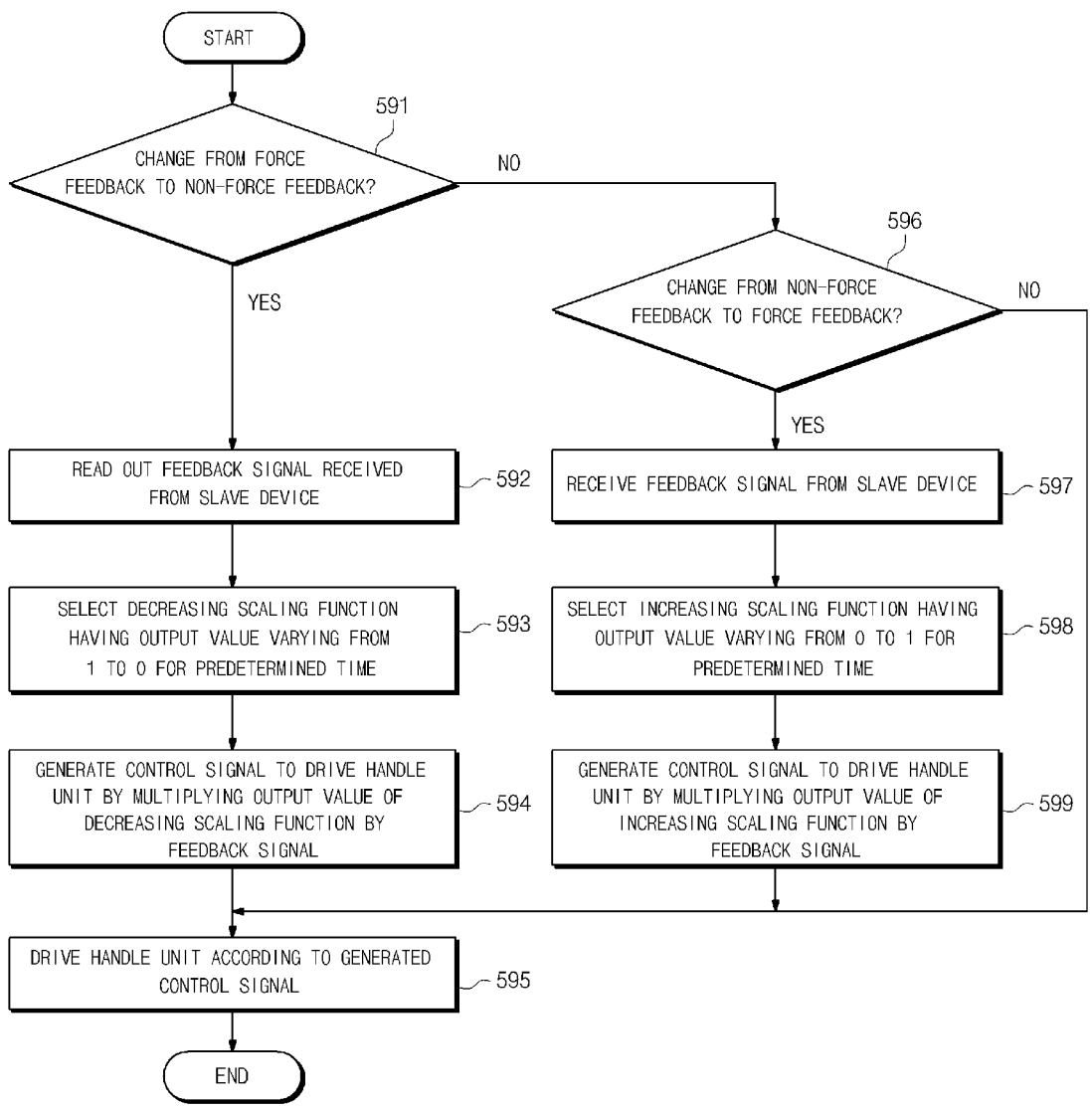
FIG. 9 is a flowchart illustrating Operation 590 of FIG. 8 in more detail.

FIG. 9 is a flowchart illustrating Operation 590 of FIG. 8 in more detail.

It may be judged or determined whether or not an operation mode of the surgical robot is changed from a force feedback mode to a non-force feedback mode (591).

If the judged result of Operation 591 shows that the operation mode is changed from a force feedback mode to a non-force feedback mode, a feedback signal received from the slave device 200 may be read out (592).

Next, a decreasing scaling function, an output value of which varies from 1 to 0 for a predetermined time, may be selected (593). For example, the selected decreasing scaling function may be preset. For example, one of the decreasing scaling functions illustrated in FIGS. 4A and 4B may be selected. The decreasing scaling function may be preset by a user.

Thereafter, a control signal to drive the handle units 141a and 141b may be generated by multiplying an output value of the decreasing scaling function with the feedback signal (594).

The generated control signal may be transmitted to the first drive unit 180, and the first drive unit 180 may drive the handle units 141a and 141b according to the control signal (595).

The above-described Operations 594 and 595 may be repeatedly performed until the output value becomes 0.

As described above, when performing the mode change process using the decreasing scaling function, the magnitude of force fed back to the handle units 141a and 141b gradually decreases for a predetermined time. Accordingly, the operator D may be ready for the end of the force feedback mode, and it may be possible to prevent unintentional movement of the handle units 141a and 141b.

If the judged result of Operation 596 shows that an operation mode is changed from a non-force feedback mode to a force feedback mode (Yes in Operation 596), a feedback signal from the slave device 200 may be received (597).

Next, an increasing scaling function, an output value of which varies from 0 to 1 for a predetermined time, may be selected (598). For example, the selected increasing scaling function may be preset. For example, one of the increasing scaling functions illustrated in FIGS. 5A and 5B may be selected. The increasing scaling function may be preset by a user.

Thereafter, a control signal to drive the handle units 141a and 141b may be generated by multiplying an output value of the increasing scaling function with the feedback signal (599).

The generated control signal may be transmitted to the first drive unit 180, and the first drive unit 180 may drive the handle units 141a and 141b according to the control signal (595).

The above-described Operations 599 and 595 may be repeatedly performed until the output value becomes 1.

As described above, when performing the mode change process using the increasing scaling function, the magnitude of force fed back to the handle units 141a and 141b gradually increases for a predetermined time. Accordingly, the operator D may be ready for the initiation of the force feedback mode, and it may be possible to prevent unintentional movements of the handle units 141a and 141b.

Although not illustrated in the drawing, an alarm may be output starting from initiation to end of the mode change process. The alarm may be visually output, or output by sound, or output by tactile feedback, or by combinations thereof.

The example embodiments of the surgical robot have been described above. The embodiments describe the case in which the mode change process is performed by the master device 100. In another embodiment, the mode change process may be performed by the slave device 200. In this case, the mode change processor 157 included in the first controller 150 of FIG. 6 may be omitted, and the second controller 250 of FIG. 7 may include a mode change processor. That is, when a mode change occurs, the master device 100 may inform the slave device 200 occurrence of mode change, and the slave device 200 may generate a control signal to be fed back to the master device 100 using a scaling function.

While the disclosure herein has provided example embodiments of a surgical robot and control method to control the surgical robot, for example, in a medical setting to perform an operation on a patient (e.g., a human or animal or other lifeform), the disclosure is not so limited. For example, the surgical robot may be used in other settings which may benefit from the surgical robot disclosed herein. For example, the surgical robot may be utilized to perform operations in any confined space or enclosure in which an operator may need to perform controlled movements using an instrument attached to a robot arm, so as to avoid or to prevent injuries to bodies or objects, that may be located or disposed within the space or enclosure, due to imprecise movements of the surgical robot. Possible settings may include, for example, mining operations, surveillance operations, inspection operations, repair operations, bomb disposal operations, etc., however again, the disclosure is not so limited.

The apparatus and methods for controlling a configuration or operation mode of the surgical robot according to the above-described example embodiments may use one or more processors, which may include a microprocessor, central processing unit (CPU), digital signal processor (DSP), or application-specific integrated circuit (ASIC), as well as portions or combinations of these and other processing devices.

The terms "module", and "unit," as used herein, may refer to, but are not limited to, a software or hardware component or device, such as a Field Programmable Gate Array (FPGA) or Application Specific Integrated Circuit (ASIC), which performs certain tasks. A module or unit may be configured to reside on an addressable storage medium and configured to execute on one or more processors. Thus, a module or unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules/units may be combined into fewer components and modules/units or further separated into additional components and modules.

Some example embodiments of the present disclosure can also be embodied as a computer readable medium including computer readable code/instruction to control at least one component of the above-described example embodiments. The medium may be any medium that can storage and/or transmission the computer readable code.

The computer readable code may be recorded in the medium, or may be transmitted via Internet. The medium, for example, may include read-only memory (ROM), random-access memory (RAM), compact disc (CD)-ROMs, magnetic tapes, floppy disks, optical data storage devices, and carrier waves such as data transmission through the Internet. The medium can also be a distributed over network coupled computer systems so that the computer readable code is stored and executed in a distributed fashion. In addition, examples of the component may include a processor or a computer processor. The element to be processed may be distributed and/or included in a single device. Some or all of the operations performed by the surgical robot according to the above-described example embodiments may be performed over a wired or wireless network.

As is apparent from the above description, upon operation mode change, it may be possible to prevent an unintentional movement of handle units or other input device of a master device by gradually varying the magnitude of force fed back to the handle units or other input device for a predetermined time.

Preventing unintentional movement of the handle units or other input device of the master device may ensure safety of a patient and/or assist in precise and accurate movement of a surgical tool or instrument when performing a task or operation using a surgical robot.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

While example embodiments have been particularly shown and described, it will be understood by those of ordinary skilled in the art that various changes in form and details may be made therein without departing from the spirit and scope of the present invention as defined by the following claims.

What is claimed is:

1. A surgical robot, comprising:
a master device having an input unit;
a slave device having at least one robotic surgical instrument configured to be remotely controlled by the master device; and
a controller configured to perform a mode change process to gradually vary a strength of a feedback signal fed back from the slave device to the input unit for a predetermined time when a signal for change of an operation mode is input via the input unit;
wherein the operation mode includes a force feedback mode that feeds back force generated in the at least one robotic surgical instrument via interaction with an external environment to the master device, and a non-force feedback mode that does not feed back the force generated in the at least one robotic surgical instrument to the master device, and
wherein the controller is further configured to gradually decrease the strength of the feedback signal fed back to the input unit for the predetermined time using a decreasing scaling function if the operation mode is changed from the force feedback mode to the non-force feedback mode.

2. The surgical robot according to claim 1, wherein an output value of the decreasing scaling function is configured to vary from 1 to 0 for the predetermined time.

3. The surgical robot according to claim 1, wherein the decreasing scaling function is selectable by an operator of the surgical robot from among a plurality of pre-stored decreasing scaling functions.

4. The surgical robot according to claim 1, wherein the predetermined time is changeable by an operator of the surgical robot.

5. The surgical robot according to claim 1, wherein the predetermined time varies according to the strength of the feedback signal fed back to the input unit.

6. The surgical robot according to claim 1, wherein the decreasing scaling function is non-linear.

7. The surgical robot according to claim 1, wherein the controller is included in the master device or the slave device.

8. A surgical robot, comprising:
a master device having an input unit;
a slave device having at least one robotic surgical instrument configured to be remotely controlled by the master device; and
a controller configured to perform a mode change process to gradually vary a strength of a feedback signal fed back from the slave device to the input unit for a predetermined time when a signal for change of an operation mode is input via the input unit;
wherein the operation mode includes a force feedback mode that feeds back force generated in the at least one robotic surgical instrument via interaction with an external environment to the master device, and a non-force feedback mode that does not feed back the force generated in the at least one robotic surgical instrument to the master device,
wherein the controller is further configured to gradually increase the strength of the feedback signal fed back to the input unit for the predetermined time using an increasing scaling function if the operation mode is changed from the non-force feedback mode to the force feedback mode, and
wherein the predetermined time varies according to the strength of the feedback signal fed back to the input unit.

9. The surgical robot according to claim 8, wherein an output value of the increasing scaling function is configured to vary from 0 to 1 for the predetermined time.

10. The surgical robot according to claim 8, wherein the increasing scaling function is selectable by an operator of the surgical robot from among a plurality of pre-stored increasing scaling functions.

11. The surgical robot according to claim 8, wherein the predetermined time is changeable by an operator of the surgical robot.

12. The surgical robot according to claim 8, wherein the increasing scaling function is non-linear.

13. A surgical robot control method for a surgical robot including a master device and a slave device, the method comprising:
generating a control signal to control at least one robotic surgical instrument provided in the slave device;
transmitting the control signal to the slave device; and
performing a mode change process to gradually vary a strength of a feedback signal fed back from the slave device to the master device for a predetermined time when an operation mode is changed;
wherein the operation mode includes a force feedback mode that feeds back force generated in the at least one robotic surgical instrument via interaction with an external environment to the master device, and a non-force feedback mode that does not feed back the force generated in the at least one robotic surgical instrument to the master device, and
wherein performing the mode change process includes gradually decreasing the strength of the feedback signal fed back from the slave device to the master device for the predetermined time using a decreasing scaling function if the operation mode is changed from the force feedback mode to the non-force feedback mode.

14. A robot, comprising:
a slave device having at least one instrument;
a master device configured to remotely perform an operation using the at least one instrument via the slave device; and
a controller configured to determine whether a change in a feedback mode is requested, and configured to perform a feedback mode change process by temporarily applying a scaling function to a feedback signal fed back from the slave device to the master device in response to the requested change in the feedback mode;
wherein the feedback mode includes a force feedback mode that feeds back force generated in the at least one instrument via interaction with an external environment to the master device, and a non-force feedback mode that does not feed back the force generated in the at least one instrument to the master device, and wherein the controller is further configured to gradually decrease a strength of the feedback signal fed back from the slave device to the master device using a decreasing scaling function if the feedback mode is changed from the force feedback mode to the non-force feedback mode.

* * * * *